US012593851B2

(12) United States Patent
Lefebvre et al.

(10) Patent No.: US 12,593,851 B2
(45) Date of Patent: Apr. 7, 2026

(54) LEAVENING AGENTS

(71) Applicant: PURATOS NV, Groot-Bijgaarden (BE)

(72) Inventors: Coralie Lefebvre, Huy (BE); Sylvestre Awono, Brussels (BE); Bernard Genot, Vieux-Waleffe (BE)

(73) Assignee: Puratos NV, Groot-Bijgaarden (BE)

( * ) Notice: Subject to any disclaimer, the term of this patent is extended or adjusted under 35 U.S.C. 154(b) by 755 days.

(21) Appl. No.: 15/759,133

(22) PCT Filed: Oct. 4, 2016

(86) PCT No.: PCT/EP2016/073655
§ 371 (c)(1),
(2) Date: Mar. 9, 2018

(87) PCT Pub. No.: WO2017/060230
PCT Pub. Date: Apr. 13, 2017

(65) Prior Publication Data
US 2019/0053502 A1 Feb. 21, 2019

(30) Foreign Application Priority Data
Oct. 6, 2015 (BE) .................................. 2015/5632

(51) Int. Cl.
| | |
|---|---|
| *A21D 8/04* | (2006.01) |
| *C12N 1/14* | (2006.01) |
| *C12N 1/145* | (2026.01) |
| *C12N 1/16* | (2006.01) |
| *C12R 1/645* | (2006.01) |

(52) U.S. Cl.
CPC ............. *A21D 8/047* (2013.01); *C12N 1/145* (2021.05); *C12N 1/16* (2013.01); *C12R 2001/645* (2021.05)

(58) Field of Classification Search
CPC ........... A21D 8/047; C12R 1/645; C12N 1/16
See application file for complete search history.

(56) References Cited

U.S. PATENT DOCUMENTS

| | | | | |
|---|---|---|---|---|
| 3,713,844 A | * | 1/1973 | Sternberg ................. | A21D 2/38 426/27 |
| 5,700,684 A | | 12/1997 | Ehret | |
| 2006/0257529 A1 | * | 11/2006 | Sommer .............. | C12G 1/0203 426/62 |

FOREIGN PATENT DOCUMENTS

| | | | | |
|---|---|---|---|---|
| EP | 0461725 A1 | 12/1991 | | |
| WO | WO-2005060757 A1 | * | 7/2005 | ............. A21D 8/042 |
| WO | WO-2011003893 A1 | * | 1/2011 | ................ C12P 7/10 |

OTHER PUBLICATIONS

CP Kurtzman, "Phylogenetic circumscription of *Saccharomyces, Kluyveromyces,* and other members of the *Saccharomycesceae,* and the proposal of the new genera Lachancea, Nakaseomyces, Naumovia, Vanderwaltozyma, and Zygotorulaspora", 2003 (no month), FEMS Yeast Research, 4, pp. 233-245. (Year: 2003).*

Canibe et al., "Microbiological and biochemical characterization of fermented liquid feed samples from 40 Danish farms", 2010 (no month), Livestock Science, 134, pp. 158-161. (Year: 2010).*

Fell et al., "The Yeasts, A taxonomic study", 2011 (no month), Elsevier, Fifth Edition, vol. 1, pp. 516-518. (Year: 2011).*

Vrancken et al. "Yeast species composition differs between artisan bakery and spontaneous laboratory sourdoughs," Apr. 2010, FEMS Yeast Res., 10, pp. 471-481 (Year: 2010).*

Urien et al., Microbial Species Diversity in French Traditional Organic Bread Doughs, Aug. 2013, retrieved from the Internet https://www.researchgate.net/publication/281097805_Microbial_species_diversity_in_French_traditional_organic_bread_doughs (Year: 2013).*

Coda et al. (Jul. 4, 2013) "Influence of particle size on bioprocess induced changes on technological functionality of wheat bran," Food Microbiology. 37:69-77.

Cossignani et al. (1996) "The sourdough microflora: Microbiological, biochemical and breadmaking characteristics of doughs fermented with freeze-dried mixed starters, freeze-dried wheat sourdough and mixed fresh-cell starters," Zeitschrift für Lebensmittel-Untersuchung und -Forschung 203:88-94.

De Vuyst et al. (Jun. 18, 2013) "Microbial ecology of sourdough fermentations: diverse or uniform?" Food Microbiology. 37:11-29.

Gobbetti et al. (1995) "Volatile compound and organic acid productions by mixed wheat sour dough starters: Influence of fermentation parameters and dynamics during baking," Food Microbiology. 12:497-507.

Gori et al. (2010) "Occurrence and identification of yeast species in fermented liquid feed for piglets," Microbial Ecology. 61(1):146-153.

Moon et al. (Apr. 1, 2014) "Pichia kudriavzevii is the major yeast involved in film-formation, off-odor production, and texture-softening in over-ripened Kimchi," Food Science and Biotechnology. 23(2):489-497.

Takakuwa et al. (2007) "Sequence analysis of the α-galactosidase MEL gene governing the efficient production of ethanol from raffinose-rich molasses in the yeast Lachancea thermotolerans," World Journal of Microbiology and Biotechnology. 23(4):587-591.

International Preliminary Report on Patentability corresponding to International Patent Application No. PCT/EP2016/073655, completed Dec. 12, 2017.

International Search Report with Written Opinion corresponding to International Patent Application No. PCT/EP2016/073655, mailed Jan. 25, 2017.

(Continued)

*Primary Examiner* — Emily M Le
*Assistant Examiner* — Tynesha L McClain
(74) *Attorney, Agent, or Firm* — Lathrop GPM LLP; James Velema; Judith Stone-Hulslander

(57) ABSTRACT

The present invention relates to compositions and methods for preparing such compositions, the compositions comprising cereal hydrolysates fermented by one or more strain(s) of the genus *Kazachstania* and/or *Lachancea*, and in particular *Kazachstania bulderi, Kazachstania exigua* and/or *Lachancea thermotolerans*. The compositions are used in the preparation of bakery and/or patisserie products.

24 Claims, 2 Drawing Sheets

(56)  References Cited

OTHER PUBLICATIONS

Lhomme, et al., "Sourdough microbial community dynamics: An analysis during French organic bread-making processes", Food Microbiology, 2016, vol. 53, pp. 41-50.

Coda et al., "Influence of particle size on bioprocess induced changes on technological functionality of wheat bran", Food Microbiology, 2014, vol. 37, pp. 69-77.

Hino et al., "New Freeze-Tolerant Yeast for Frozen Dough Preparations", Cereal Chemistry, 1987, vol. 64, No. 4, pp. 269-275.

"*Saccharomyces cerevisiae* Meyen ex E.C. Hansen (1883)", The Yeast: a taxonomic study, 2011, Chapter 61, Part IVB, pp. 373-740.

Kazachstania aerobia Lu, Cai, Wu, Jia & Bai (2004b), The Yeast: a taxonomic study, 2011, Chapter 34, Part IVB, pp. 441-447.

Bonjean et al., "Yeasts in bread and baking products", Chapter 11, Yeasts in Food—Beneficial and Detrimental Aspects, 2003, edited by Boekhout & Robert, pp. 289-307.

Kurtzman et al., "Phylogenetic relationships among yeasts of the '*Saccharomyces* complex' determined from multigene sequence analyses", FEMS Yeast Research, Jun. 2003, 3(4): 417-432.

Wikipedia section on Brewer's Yeast, page last edited on Jul. 13, 2022, obtained from url: <https://en.wikipedia.org/wiki/Yeast#Beer> on Aug. 29, 2022.

Fleet, "Yeast Spoilage of Foods and Beverages," The Yeasts, 2011, Chapter 5, pp. 53-63.

James et al., "Spoilage yeasts with emphasis on the genus Zygosaccharomyces," Yeasts in Food, 2003, Chapter 6, pp. 171-191.

Kabisch et al., "Spoilage of vacuum-packed beef by the yeast Kazachstania psychrophila," Food Microbiology, 2016, 53(Pt. B): 15-23 (published ahead of print online Aug. 15, 2015 ).

Kurtzman et al., "Index to taxa by genus and species," The Yeasts, a Taxonomic Study, 5th Ed., 2011, pp. i1-i22.

Lu et al., "*Kazachstania aerobia* sp. Nov., ascomycetous yeast species from aerobically deteriorating corn silage," International Journal of Systemic and Evolutionary Microbiology, 2004, 54: 2431-2435.

Snowdon et al., "Mousy Off-Flavor," Agricultural and Food Chemistry, 2006, 54(18): 6465-6474.

* cited by examiner

LEAVENING AGENTS

CROSS-REFERENCE TO RELATED APPLICATIONS

This application is a 35 U.S.C. § 371 filing of International Patent Application No. PCT/EP2016/073655, filed Oct. 4, 2016, which claims priority to Belgium Application No. 2015/5632, filed Oct. 6, 2015, the entire contents of which are incorporated herein by reference.

FIELD OF THE INVENTION

The present invention relates to non-conventional leavening agents and baked products obtained with said leavening agents.

BACKGROUND OF THE INVENTION

Today bread consumers are constantly looking for new products having innovative or improved properties. Among these are the aroma and the taste of particular relevance.

The leavening of baked products such as breads is usually performed using the yeast *Saccharomyces cerevisiae* as leavening agent. Through fermentation of the dough the yeast produces $CO_2$ and allows it to rise. This gives also to the baked product its aerated structure. Baked products obtained by the use of *Saccharomyces cerevisiae* tend to have poor taste and aroma due inter alia to the short processing times used.

Sourdough fermentations are well-known alternative baking techniques that are used to improve the aroma and taste of breads. Typical tastes/aromas given by sourdough are lactic, acetic, toasted, fruity, fermented or cereal. Sourdoughs are generally obtained by the fermentation of cereals or cereal flours by strains of lactic acid bacteria and/or baker's yeast. Lactic acid bacteria isolated from sourdoughs are mainly *Lactobacillus, Leuconostoc, Pediococcus* and *Streptococcus*, but the majority belongs to the *Lactobacillus* group. Lactic acid bacteria fermentation generates lactic acid and/or acetic acid that give the acidity to the sourdough. *Saccharomyces cerevisiae* is the most frequent yeast species in conventional sourdough. Other species of *Saccharomyces, Candida, Pichia* and *Hansenula* have occasionally been isolated and used.

Most of the breads based on sourdough have typical tastes and aromas mainly due to the acidic environment. However the consumer does not always accept/eat breads with such typical tastes and aromas.

Other alternative baking techniques are based on the use of leavening agents obtained through the fermentation of non-conventional substrates such as cereal hydrolysates. However, the use of non-conventional substrates such as cereal hydrolysates in the preparation of leavening agents with conventional yeasts such as *Saccharomyces cerevisiae* gives breads that have a poor aroma and an unpleasant aftertaste.

Therefore there is still a need to find alternative compositions and methods to obtain breads with improved taste and aroma.

It is therefore the aim of the present invention to provide breads with new typical aromas and tastes. Accordingly the present invention provides new leavening agents and methods to use said new leavening agents.

SUMMARY OF THE INVENTION

The inventors have surprisingly found that it was possible to obtain bakery products such as breads with improved taste and aroma by using strains of *Kazachstania* and/or *Lachancea* and in particular *Kazachstania bulderi, Kazachstania exigua* and/or *Lachancea thermotolerans* as leavening agent. More specifically, it has been found that by fermenting cereal hydrolysates with *Kazachstania* and/or *Lachancea* and in particular *Kazachstania bulderi, Kazachstania exigua* and/or *Lachancea thermotolerans*, it was possible to prepare leavening agents that prevent the apparition of off-flavors during baking that are usually obtained when using leavening agents based on cereal hydrolysates fermented by the classical baker's yeast *Saccharomyces cerevisiae*.

In a first aspect, the present invention relates to a composition comprising cereal hydrolysates, wherein said composition is fermented by one or more strain(s) of the genus *Kazachstania* and/or *Lachancea*.

In a second aspect, the present invention relates to a method for producing a composition, comprising fermenting a mixture comprising cereal hydrolysates, and a liquid with one or more strain(s) of the genus *Kazachstania* and/or *Lachancea*, thereby obtaining a composition; and optionally stabilizing and/or packaging said composition.

In particular, the composition or method respectively according to the first or second aspect of the invention as described herein, provides that at least one of said strains of the genus *Kazachstania* is a strain of *Kazachstania bulderi* or *Kazachstania exigua* and/or wherein at least one of said strains of the genus *Lachancea* is a strain of *Lachancea thermotolerans*.

In particular, the composition or method respectively according to the first or second aspect of the invention as described herein, provides that at least one of said strains of the genus *Kazachstania* is *Kazachstania bulderi* MUCL 54530 or *Kazachstania exigua* ATCC 22034 and/or wherein at least one of said strains of the genus *Lachancea* is *Lachancea thermotolerans* MUCL 55817.

In particular, the composition or method respectively according to the first or second aspect of the invention as described herein, provides that said composition comprises (a) an amount of one or more strain(s) of the genus *Kazachstania* and/or *Lachancea* ranging between about $10^8$ to $10^{10}$ cfu/ml; (b) wherein the pH of said composition ranges between about 3.8 and about 6; and/or (c) wherein the leavening power of said composition ranges between about 300 ml and about 1500 ml of $CO_2$ produced in 2 hours when measured by SJA analysis.

In particular, the composition or method respectively according to the first or second aspect of the invention as described herein, provides that said one or more strain(s) of the genus *Kazachstania* and/or *Lachancea* are combined with one or several other strain(s) of microorganisms, preferably other strain(s) of yeast and/or strains of lactic acid bacteria.

In particular, the composition or method respectively according to the first or second aspect of the invention as described herein, provides that said one or more strain(s) of the genus *Kazachstania* and/or *Lachancea* are essentially the sole $CO_2$ producing microorganism in said composition.

In particular, the composition or method respectively according to the first or second aspect of the invention as described herein, provides that said composition comprises an amylase source preferably chosen from the group of amyloglucosidase, malt active flour and alpha-amylase, wherein the source of amylase is preferably added in an amount to obtain in said composition between 1 and 30 AGU/g liquid leaven of amyloglucosidase; between 1 and 16 DU/g liquid leaven of active malt flour; or between 10 and 80 SKB/g liquid leaven of alpha-amylase.

In particular, the composition or method respectively according to the first or second aspect of the invention as described herein, provides that said cereal hydrolysates are based on durum wheat flour or durum wheat malt, on wheat flour or wheat malt, on rye flour or rye malt or on a combination of these.

In a further aspect, the present invention relates to the use of a composition as described herein as leavening agent, preferably a liquid leavening agent.

In a further aspect, the present invention relates to the use of a composition as described herein as an ingredient for the preparation of a food product, preferably a baked product, more preferably a bakery or patisserie product.

In a further aspect, the present invention relates to a baked product comprising a composition according to the present invention and as described herein, preferably a bakery or patisserie product comprising a composition to the present invention and as described herein.

In a further aspect, the present invention relates to a method for obtaining a baked product, such as a bakery or patisserie product, comprising the steps of:

providing a composition according to the present invention and as described herein;

adding the composition to a dough or a batter; and baking the dough or the batter, thereby obtaining the baked product, such as the bakery or patisserie product.

In a further aspect, the present invention relates to a *Kazachstania bulderi* strain deposited under accession number MUCL 54530 at the BCCM/MUCL (Agro)industrial Fungi & Yeasts Collection, or a *Lachancea thermotolerans* strain deposited under accession number MUCL 55817 at the BCCM/MUCL (Agro)industrial Fungi & Yeasts Collection, in particular a *Kazachstania bulderi* strain deposited under accession number MUCL 54530 at the BCCM/MUCL (Agro)industrial Fungi & Yeasts Collection.

In a further aspect, the present invention relates to the use of the *Kazachstania bulderi* strain deposited under accession number MUCL 54530 at the BCCM/MUCL (Agro)industrial Fungi & Yeasts Collection, or the *Lachancea thermotolerans* strain deposited under accession number MUCL 55817 at the BCCM/MUCL (Agro)industrial Fungi & Yeasts Collection, in particular the *Kazachstania bulderi* strain deposited under accession number MUCL 54530 at the BCCM/MUCL (Agro)industrial Fungi & Yeasts Collection, for the preparation of a food product, preferably a baked product, more preferably a bakery or patisserie product.

DETAILED DESCRIPTION

Figure 1:
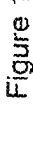
FIG. 1 shows a comparison of the content in volatile molecules obtained by SPME-GC-MS of Kb2 (rye malt flour hydrolysate fermented by Kazachstania *bulderi* MUCL 54530-lower part of the graph) and of Sc2 (rye malt flour hydrolysate fermented by *Saccharomyces cerevisiae*-upper part of the graph).

Before the present compositions, methods, uses, baked products, and strains used in the invention are described, it is to be understood that this invention is not limited to particular compositions, methods, uses, baked products, and strains described, as such compositions, methods, uses, baked products, and strains may, of course, vary. It is also to be understood that the terminology used herein is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any method and material similar or equivalent to those described herein may be used in practice or testing of the present invention, the preferred methods and materials are now described.

In this specification and the appended claims, the singular forms "a", "an", and "the" include plural references unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

The recitation of numerical ranges by endpoints includes all numbers and fractions subsumed within the respective ranges, as well as the recited endpoints.

The inventors have surprisingly found that it was possible to obtain bakery products such as breads with improved taste and aroma by using strains of *Kazachstania* and/or *Lachancea* and in particular *Kazachstania bulderi, Kazachstania exigua* and/or *Lachancea thermotolerans* as leavening agent. More specifically, it has been found that by fermenting cereal hydrolysates with *Kazachstania* and/or *Lachancea* and in particular *Kazachstania bulderi, Kazachstania exigua* and/or *Lachancea thermotolerans*, it was possible to prepare leavening agents that prevent the apparition of off-flavors during baking that are usually obtained when using leavening agents based on cereal hydrolysates fermented by the classical baker's yeast *Saccharomyces cerevisiae*.

The inventors have found that it was possible to obtain bakery products such as breads with improved taste and aroma by using strains of *Kazachstania* and in particular *Kazachstania bulderi* and/or *Kazachstania exigua* as leavening agent. More specifically, it has been found that by fermenting cereal hydrolysates with *Kazachstania* and in particular *Kazachstania bulderi* and/or *Kazachstania exigua*, it was possible to prepare leavening agents that prevent the apparition of off-flavors during baking that are usually obtained when using leavening agents based on cereal hydrolysates fermented by the classical baker's yeast *Saccharomyces cerevisiae*.

Therefore in a first aspect the present invention provides in a composition comprising one or more strain(s) of the genus *Kazachstania* and/or *Lachancea*, in particular one or more strain(s) of the genus *Kazachstania*.

More in particular, the composition according to the present invention comprises cereal hydrolysates, wherein said composition is fermented by one or more strain(s) of the genus *Kazachstania* and/or *Lachancea*.

In certain embodiments, the composition as taught herein may be fermented by at least one strain of the genus *Kazachstania*, such as at least two strains, at least three strains, at least four strains, at least five strains, at least six strains, at least seven strains, at least eight strains, or at least nine strains of the genus *Kazachstania*.

In certain embodiments, the composition as taught herein may be fermented by at least one strain of the genus *Lachancea*, such as at least two strains, at least three strains, at least four strains, at least five strains, at least six strains, at least seven strains, at least eight strains, or at least nine strains of the genus *Lachancea*.

In certain embodiments, the method as taught herein may provide in the fermentation by at least one strain of the genus *Kazachstania*, such as at least two strains, at least three strains, at least four strains, at least five strains, at least six strains, at least seven strains, at least eight strains, or at least nine strains of the genus *Kazachstania*.

In certain embodiments, the method as taught herein may provide in the fermentation by at least one strain of the genus *Lachancea*, such as at least two strains, at least three strains, at least four strains, at least five strains, at least six strains, at least seven strains, at least eight strains, or at least nine strains of the genus *Lachancea*.

In certain embodiments of the compositions, methods, uses, or baked products, as taught herein, said at least one strain of the genus *Kazachstania* may be selected from the group consisting of *Kazachstania aerobia, Kazachstania africana, Kazachstania aquatica, Kazachstania bamettii, Kazachstania bovina, Kazachstania bulderi, Kazachstania exigua, Kazachstania gamospora, Kazachstania hellenica, Kazachstania heterogenica, Kazachstania humatica, Kazachstania jiainica, Kazachstania kunashirensis, Kazachstania lodderae, Kazachstania martiniae, Kazachstania naganishii, Kazachstania piceae, Kazachstania pintolopesii, Kazachstania rosinii, Kazachstania servazzii, Kazachstania siamensis, Kazachstania sinensis, Kazachstania slooffiae, Kazachstania solicola, Kazachstania spencerorum, Kazachstania telluris, Kazachstania transvaalensis, Kazachstania turicensis, Kazachstania unispora, Kazachstania viticola, Kazachstania wufongensis, Kazachstania yakushimaensis* and/or *Kazachstania zonata*.

In certain embodiments of the compositions, methods, uses, or baked products, as taught herein, said at least one strain of the genus *Lachancea* may be selected from the group consisting of *Lachancea cidri, Lachancea dasiensis, Lachancea fermentati, Lachancea kluyveri, Lachancea lanzarotensis, Lachancea meyersii, Lachancea nothofagi, Lachancea* sp. CFL-2008, *Lachancea* sp. ES12S06, *Lachancea* sp. FDE82, *Lachancea* sp. GJ3L14, *Lachancea* sp. MC-SPC2(7), *Lachancea* sp. PJ-2012a, *Lachancea* sp. PJ-2012b, *Lachancea* sp. SC5L02, *Lachancea* sp. SC6L01, *Lachancea* sp. SW109, *Lachancea* sp. UCLM 24A, *Lachancea* sp. UCLM 88.3C, *Lachancea* sp. UWOPS 79-139, *Lachancea* sp. UWOPS 99-807.3, *Lachancea* sp. Y309, *Lachancea thermotolerans* and/or *Lachancea waltii*.

More in particular, the compositions, methods, uses, or baked products, as described herein provide that at least one of said strains of the genus *Kazachstania* is a strain of *Kazachstania bulderi* or *Kazachstania exigua* and/or wherein at least one of said strains of the genus *Lachancea* is a strain of *Lachancea thermotolerans*. In particular said strain of the genus *Kazachstania* is a strain of *Kazachstania*

*bulderi*. In particular said strain of the genus *Kazachstania* is a strain of *Kazachstania exigua*.

More in particular, the compositions, methods, uses, or baked products, as described herein provide that at least one of said strains of the genus *Kazachstania* is *Kazachstania bulderi* MUCL 54530 or *Kazachstania exigua* ATCC 22034 and/or wherein at least one of said strains of the genus *Lachancea* is *Lachancea thermotolerans* MUCL 55817. In particular said strain of the genus *Kazachstania* is *Kazachstania bulderi* MUCL 54530. In particular said strain of the genus *Kazachstania* is *Kazachstania exigua* ATCC 22034.

*Kazachstania bulderi* MUCL 54530 refers to the *Kazachstania bulderi* strain deposited under accession number MUCL 54530 on Jan. 8, 2013 at the BCCM/MUCL (see Table A1). *Kazachstania exigua* ATCC 22034 refers to the *Kazachstania exigua* strain available at the American Type Culture Collection under catalogue number ATCC 22034.

*Lachancea thermotolerans* MUCL55817 refers to the *Lachancea thermotolerans* strain deposited under accession number MUCL55817 on 18 Aug. 2015 at the BCCM/MUCL (see Table A2).

Biological material deposited with the Belgian Coordinated Collections of Microorganisms (BCCM/MUCL) has been accepted for deposit under the Budapest Treaty on the International Recognition of the Deposit of Microorganisms for the purpose of Patent Procedure. All restrictions on the availability to the public of the material deposited will be irrevocably removed upon the granting of the instant application.

The recitation "fermented by" as used herein refers to fermentation in the presence of the disclosed strains. For instance, "fermented by" may comprise fermentation in the presence of the disclosed strains for at least 24 h, for at least 48 h, for at least 72 hours, for at least 96 hours, for at least 120 hours, for at least 144 hours, or for at least 192 hours.

In a particular embodiment, the composition as described herein is a leavening agent, and in particular a liquid leavening agent.

The term "leavening agent" as used in the context of the present invention refers to a composition able to produce at least part of the $CO_2$, and preferably essentially all the $CO_2$, needed to achieve a good rising of a dough during the fermentation step(s) before baking. Leavening agents may also be referred to as preferments, sponges (yeast sponges), starters (yeast-based starters), biga, etc.

The composition, preferably leavening agent, as described in the present invention is obtained by the fermentation of cereal hydrolysate(s). The term "cereal hydrolysate" as used in the context of the present invention, refers to product(s) that result(s) from the enzymatic hydrolysis of an aqueous dispersion of a cereal or of a cereal fraction. Hydrolytic enzymes are generally amylases, beta-amylases, beta-glucanases and/or pentosanases and optionally proteases. Cereal hydrolysates may be under liquid or powder (dried) form.

The term "cereal", in the context of the present invention, refers to the edible components of plants of the botanical family of the Poaceae, including but not limited to species such as wheat, durum wheat, barley, oat, spelt, rye, sorghum, maize, triticale, millet, teff and/or rice. Preferably, the cereals are chosen among the group of wheat, durum wheat or rye. A more preferred cereal is rye or durum wheat. The term "cereal" includes also malted cereals.

In a particular embodiment, the compositions, methods, uses, or baked products, as described herein provide that said cereal hydrolysates are based on durum wheat flour or durum wheat malt, on wheat flour or wheat malt, on rye flour or rye malt or on a combination of these.

The term "cereal fraction", in the context of the present invention, refers to all or part of the fractions resulting from mechanical reduction of the size of grains, through, as examples but not limited to, cutting, rolling, crushing, breakage or milling, with or without fractionation, through, as examples but not limited to, sieving, screening, sifting, blowing, aspirating, centrifugal sifting, wind sifting, electrostatic separation, or electric field separation. Preferred cereal fractions are flours, whole flours, brans and/or any combination thereof.

Preferably the cereal hydrolysate(s) used in the present invention is(are) based on durum wheat flour or durum wheat malt, on wheat flour or wheat malt, on rye flour or rye malt or on a combination of these.

In a particular embodiment, the compositions, methods, uses, or baked products, as described herein provide that said composition comprises (a) an amount of one or more strain(s) of the genus *Kazachstania* and/or *Lachancea*, preferably *Kazachstania bulderi, Kazachstania exigua* and/or *Lachancea thermotolerans* and more preferably *Kazachstania bulderi* MUCL 54530, *Kazachstania exigua* ATCC 22034 and/or *Lachancea thermotolerans* MUCL 55817, ranging between about $10^8$ to $10^{10}$ cfu/ml;

(b) wherein the pH of said composition ranges between about 3.8 and about 6; and/or (c) wherein the leavening power of said composition ranges between about 300 ml and about 1500 ml, preferably between about 600 ml and about 1300 ml, of $CO_2$ produced in 2 hours when measured by SJA analysis.

In a particular embodiment, the compositions, methods, uses, or baked products, as described herein provide that said composition comprises (a) an amount of one or more strain(s) of the genus *Kazachstania*, preferably *Kazachstania bulderi* and/or *Kazachstania exigua* and more preferably *Kazachstania bulderi* MUCL 54530 and/or *Kazachstania exigua* ATCC 22034, ranging between about $10^8$ to $10^{10}$ cfu/ml;

(b) wherein the pH of said composition ranges between about 3.8 and about 6; and/or (c) wherein the leavening power of said composition ranges between about 300 ml and about 1500 ml, preferably between about 600 ml and about 1300 ml, of $CO_2$ produced in 2 hours when measured by SJA analysis.

In particular, the amount of *Kazachstania bulderi* ranges between about $10^8$ to $10^{10}$ cfu/ml in the compositions according to the present invention. In particular, the amount of *Kazachstania exigua* ranges between about $10^8$ to $10^{10}$ cfu/ml in the compositions according to the present invention. In particular, the amount of *Lachancea thermotolerans* ranges between about $10^8$ to $10^{10}$ cfu/ml in the compositions according to the present invention. The leavening power of the compositions according to the present invention may be advantageously measured by a SJA analysis. In this method, a dough is made with 280 g of wheat flour, leavening agent or yeast in an amount corresponding to 1.37 g of yeast dry matter, 5.04 g of NaCl, 0.75 AGU/g flour of amyloglucosidase and water up to a total dough hydration level of 35%. The dough is mixed during 6 minutes in a farinograph (SCHMERSAL) at 30° C. Then 300 g of dough are introduced in a SJA fermentograph (Mekab machine, Mekab i Nässjö AB) chamber at 37° C. The analysis lasts for 2 hours.

The result of the analysis is expressed by the addition of the volume of $CO_2$ produced during the first hour and the volume of $CO_2$ produced during the second hour.

In a particular embodiment, the compositions, methods, uses, or baked products, as described herein provide that said one or more strain(s) of the genus *Kazachstania* and/or *Lachancea*, preferably *Kazachstania bulderi, Kazachstania exigua* and/or *Lachancea thermotolerans* and more preferably *Kazachstania bulderi* MUCL 54530, *Kazachstania exigua* ATCC 22034 and/or *Lachancea thermotolerans* MUCL 55817, are combined with one or several other strain(s) of microorganisms, preferably other strain(s) of yeast and/or strains of lactic acid bacteria.

In a particular embodiment, the compositions, methods, uses, or baked products, as described herein provide that said one or more strain(s) of the genus *Kazachstania*, preferably *Kazachstania bulderi* and/or *Kazachstania exigua* and more preferably *Kazachstania bulderi* MUCL 54530 and/or *Kazachstania exigua* ATCC 22034, are combined with one or several other strain(s) of microorganisms, preferably other strain(s) of yeast and/or strains of lactic acid bacteria.

In a particular embodiment, the compositions, methods, uses, or baked products, as described herein provide that said one or more strain(s) of the genus *Kazachstania* and/or *Lachancea*, preferably *Kazachstania bulderi, Kazachstania exigua* and/or *Lachancea thermotolerans* and more preferably *Kazachstania bulderi* MUCL 54530, *Kazachstania exigua* ATCC 22034 and/or *Lachancea thermotolerans* MUCL 55817, are essentially the sole $CO_2$ producing microorganism in said composition.

In a particular embodiment, the compositions, methods, uses, or baked products, as described herein provide that said one or more strain(s) of the genus *Kazachstania*, preferably *Kazachstania bulderi* and/or *Kazachstania exigua* and more preferably *Kazachstania bulderi* MUCL 54530 and/or *Kazachstania exigua* ATCC 22034, are essentially the sole $CO_2$ producing microorganism in said composition.

In particular embodiments the strains of *Kazachstania bulderi, Kazachstania exigua* and/or *Lachancea thermotolerans* may be combined with one or several other strain(s) of microorganisms. Preferably these other strain(s) of microorganisms are chosen among other strain(s) of yeast or among strains of lactic acid bacteria. More preferably, these other strains of microorganisms are strains known in the art.

In particular embodiments, the strains of *Kazachstania bulderi, Kazachstania exigua* and/or *Lachancea thermotolerans* are the sole living microorganisms or sole $CO_2$ producing microorganisms in the composition according to the present invention.

In particular embodiments the composition according to the present invention may be liquid, compressed or dried. Preferably the composition is a liquid composition, preferably a liquid preferment or a liquid sponge. Preferred dry matter of the liquid composition is between 6 and 13.5 wt %.

In a particular embodiment, the compositions, methods, uses, or baked products, as described herein provide that said composition comprises an amylase source. Preferably the amylase source is chosen from the group comprising amyloglucosidase, malt active flour and alpha-amylase, more preferably amyloglucosidase or malt active flour and even more preferably amyloglucosidase.

In a particular embodiment the source of amylase is added in an amount to obtain in said composition:

between 1 and 30 AGU/g liquid leaven of amyloglucosidase; preferably between 3 and 15 AGU/g liquid leaven of amyloglucosidase; more preferably between 3 and 7.5 AGU/g liquid leaven of amyloglucosidase; or between 1 and 16 DU/g liquid leaven of active malt flour; preferably between 2 and 8 DU/g liquid leaven of active malt flour; or between 10 and 80 SKB/g liquid leaven of alpha-amylase; preferably between 20 and 40 SKB/g liquid leaven of alpha-amylase.

The skilled person will understand that combinations of different enzymes of different types, such as amyloglucosidase and active malt flour, amyloglucosidase and alpha-amylase, active malt flour and alpha-amylase or amyloglucosidase, active malt flour and alpha-amylase are also particularly suited for the purpose of the present invention.

According to a second aspect the present invention relates to a method for producing a composition, comprising fermenting a mixture comprising cereal hydrolysates, and a liquid with one or more strain(s) of the genus *Kazachstania* and/or *Lachancea*, preferably one or more strain(s) of the genus *Kazachstania*, thereby obtaining a composition; and optionally stabilizing and/or packaging said composition.

In particular, the method for producing a composition, such as a leavening agent, as described herein typically comprises the steps of:

(a) preparing a mixture comprising a fermentation substrate comprising cereal hydrolysates, preferably essentially cereal hydrolysates, water and one or more strain (s) of the genus *Kazachstania* and/or *Lachancea*, preferably *Kazachstania bulderi*, *Kazachstania exigua* and/or *Lachancea thermotolerans* and more preferably *Kazachstania bulderi* MUCL 54530, *Kazachstania exigua* ATCC 22034 and/or *Lachancea thermotolerans* MUCL 55817; preferably preparing a mixture comprising a fermentation substrate comprising cereal hydrolysates, preferably essentially cereal hydrolysates, water and one or more strain(s) of the genus *Kazachstania*, preferably *Kazachstania bulderi* and/or *Kazachstania exigua* and more preferably *Kazachstania bulderi* MUCL 54530 and/or *Kazachstania exigua* ATCC 22034;

(b) fermenting said mixture;

(c) optionally stabilizing said fermented mixture;

(d) optionally drying said fermented mixture; and;

(e) optionally packaging said fermented mixture;

The fermentation substrate comprises or consists of essentially cereal hydrolysate(s). Preferably, the cereal hydrolysate(s) is (are) added in an amount between 5 and 10% (calculated as the weight of fermentable sugars (DP1 and DP2)/weight of the mixture at the end of the fermentation).

The term "sugar" as used herein, refers to fermentable carbohydrates with a degree of polymerization (DP) of 1 or 2, such as sucrose, glucose and compounds/products containing sucrose or glucose, such as molasses, sugar beet sugar, cane sugar and hydrolysed starches but not limited to these. In the present invention, amounts of sugar(s) refer to the sum of DP1 and DP2 as measured by methods known in the art such as HPLC.

The terms "fermentation" or "fermenting" refer to a microbial process in which bacteria (e.g., one or more strain(s) of the genus *Kazachstania* and/or *Lachancea*, preferably *Kazachstania bulderi*, *Kazachstania exigua* and/or *Lachancea thermotolerans* and more preferably *Kazachstania bulderi* MUCL 54530, *Kazachstania exigua* ATCC 22034 and/or *Lachancea thermotolerans* MUCL 55817) convert carbohydrates to carbon dioxide, organic acids, and/or alcohols. In certain embodiments, the fermentation may be an aerobic fermentation. The term "aerobic fermentation" as used herein refers to fermentation in the presence of oxygen. In certain embodiments, oxygen may be added to the (liquid) mixture by mixing the (liquid) mixture, such as by continuously mixing or by mixing at intervals, or by bubbling air or oxygen through the (liquid) mixture, such as by continuously bubbling air or oxygen through the (liquid) mixture or by bubbling air or oxygen through the (liquid) mixture at intervals.

In certain embodiments, during fermentation or incubation, the (liquid) mixture may be mixed, such as mixed continuously or at various intervals. In certain embodiments, during fermentation or incubation, air or oxygen may be bubbled through the (liquid) mixture, for instance continuously or at various intervals.

In certain embodiments, the fermentation may be performed at a temperature between 15° C. and 50° C., preferably between 25° C. and 45° C., more preferably between 25° C. and 35° C. These ranges includes temperatures of 25° C., 28° C., 30° C., 32° C., 35° C., 40° C., 45° C., and 50° C.

The fermentation conditions to obtain the compositions of the invention are conventional fermentation conditions. Fermentation is preferably conducted in a fermenter equipped with at least temperature, pH and $O_2$ level controls. The pH is maintained between 3.9 and 6, preferably around 4.8 and is set to around 3.9 at the end of fermentation; the temperature is maintained around 30° C. The fermentation may be performed in a batch, a fed-batch or a continuous mode, preferably in a fed-batch mode with gradual addition of the cereal hydrolysate(s) for about 15 hours. A skilled person in the art will know how to adapt the fermentation medium and the fermentation conditions to obtain the desired biomass at the end of the process. This may include the addition of vitamins, minerals, or other additives to obtain the desired biomass. At the end of the fermentation the composition is cooled preferably between 0° C. and 7° C., more preferably at 4° C.

It should be noted that the decantation of the composition may be avoided by regularly or continuously mixing the composition.

In a particular step according to the method as described herein, after the fermentation the composition may be stabilized by the addition of a source of amylase, In a particular step according to the method as described herein, after the fermentation the composition may be further stabilized by the addition of a gum and/or an hydrocolloid. In a preferred embodiment said gum is xanthan gum, preferably in an amount between 0.1 to 0.4%, more preferably about 0.2%.

In a particular step according to the method as described herein, after the fermentation the composition may be dried using conventional methods in the art such as fluid-bed drying (eventually preceded by a step of liquid removal such as press filtering, drum filtering and/or extrusion), freeze drying, . . . .

Preferred dry matter of the solid or powdered composition is more than 85% (w/w), preferably more than 90%, more preferably more than 92%.

In a particular step according to the method as described herein, after the fermentation the composition may be packaged in liquid form or dried form in any packaging that ensure protection and stability of the product. For dried form, package under vacuum or modified atmosphere is generally used to avoid oxidation.

In certain embodiments of the compositions, methods, uses, or baked products, as taught herein, the composition may be a liquid composition or a dried composition.

In certain embodiments of the compositions, methods, uses, or baked products, as taught herein, said composition is a leavening agent, preferably a liquid leavening agent.

In certain embodiments of the compositions, methods, uses, or baked products, as taught herein, the present invention relates to a dried composition obtained by drying a liquid composition as taught herein. The drying of the liquid composition can be performed using the typical drying techniques available to the skilled person. Preferably the dried composition is obtained through fluidization, spray-drying or by drum-drying of the liquid composition.

According to a further aspect, the present invention relates to the use of a composition as described herein as leavening agent, preferably a liquid leavening agent.

According to a further aspect, the present invention relates to the use of a composition as described herein as an ingredient for the preparation of a food product, preferably a baked product, more preferably a bakery or patisserie product. The present use of the composition improves the taste of the baked products, and at the same time provides baked products with satisfying physical properties such as satisfying volume.

In certain embodiments, the composition as taught herein may be used as part of an improver, a premix, or a complete mix for the preparation of a baked product, preferably a bakery or patisserie product.

More particularly, in certain embodiments, the present invention provides the use of a composition as defined herein as part of an improver, a premix, or a complete mix for the preparation of a baked product.

An "improver" as used herein refers to a composition comprising ingredients and/or technological aids used for their beneficial properties during the preparation of baked products and/or after baking. These properties comprise but are not limited to aspect, volume, freshness, conservation, colour, structure or short bite of the baked products.

The term "premix" as used herein refers typically to an improver composition wherein the concentration in "active" component is lower than in a bakery improver. Typically a premix is used at a higher dose than an improver (weight/ weight of flour).

The term "complete mix" as used herein refers typically to a composition comprising all the ingredients needed to prepare dough that can be baked to obtain a baked product, generally with the exception of a liquid such as water.

According to a further aspect, the present invention relates to a method for obtaining a baked product, such as a bakery or patisserie product, comprising the steps of:

providing a composition according to the present invention;

adding the composition to a dough or a batter; and baking the dough or the batter, thereby obtaining the baked product, such as the bakery or patisserie product.

Hence, a further aspect provides a method for obtaining a baked product, such as a bakery or patisserie product, comprising the steps of: providing a composition comprising a fermentation substrate comprising cereal hydrolysates fermented by at least one or more strain(s) of the genus *Kazachstania* and/or *Lachancea*, preferably *Kazachstania bulderi, Kazachstania exigua* and/or *Lachancea thermotolerans* and more preferably *Kazachstania bulderi* MUCL 54530, *Kazachstania exigua* ATCC 22034 and/or *Lachancea thermotolerans* MUCL 55817; in particular one or more strain(s) of the genus *Kazachstania*, preferably *Kazachstania bulderi* and/or *Kazachstania exigua* and more preferably *Kazachstania bulderi* MUCL 54530 and/or *Kazachstania exigua* ATCC 22034; adding the composition to a dough or a batter; and baking the dough or the batter, thereby obtaining the baked product, such as the bakery or patisserie product. The composition of dough may be as known in the art. The composition of batter may be as known in the art. A dough or batter may comprise flour derived from cereal grains, water, fat or fat replacer, sugar, eggs, gluten, starch, hydrocolloids, enzymes, emulsifiers, oxidizing or reducing compounds, prebiotic compounds, and/or an improver.

The step of baking the dough or the batter may be performed as known in the art. For instance, baking the dough or the batter may be performed by placing the dough or batter in a heated oven, for instance at 160° C. to 400° C. for 10 minutes to 4 hours depending on the type of application, but not limited to this.

In another embodiment it is provided methods to obtain new types of bread that comprises the following steps:

Prepare a dough comprising cereal(s) and/or cereal fraction(s), water and a leavening agent that comprises cereal hydrolysates, wherein said cereal hydrolysates is fermented by at least one or more strain(s) of the genus *Kazachstania* and/or *Lachancea*, preferably *Kazachstania bulderi, Kazachstania exigua* and/or *Lachancea thermotolerans* and more preferably *Kazachstania bulderi* MUCL 54530, *Kazachstania exigua* ATCC 22034 and/or *Lachancea thermotolerans* MUCL 55817; in particular one or more strain(s) of the genus *Kazachstania*, preferably *Kazachstania bulderi* and/or *Kazachstania exigua* and more preferably *Kazachstania bulderi* MUCL 54530 and/or *Kazachstania exigua* ATCC 22034; and preferably wherein said leavening agent contains amyloglucosidase in an amount to give an activity between 1 and 30 AGU/g, preferably between 3 to 15 AGU/g, even more preferably between 3 and 7.5 AGU/g or a combination of a leavening agent, that comprises cereal hydrolysates, wherein said cereal hydrolysates is fermented by at least one or more strain(s) of the genus *Kazachstania* and/or *Lachancea*, preferably *Kazachstania bulderi, Kazachstania exigua* and/or *Lachancea thermotolerans* and more preferably *Kazachstania bulderi* MUCL 54530, *Kazachstania exigua* ATCC 22034 and/or *Lachancea thermotolerans* MUCL 55817; in particular one or more strain(s) of the genus *Kazachstania*, preferably *Kazachstania bulderi* and/or *Kazachstania exigua* and more preferably *Kazachstania bulderi* MUCL 54530 and/or *Kazachstania exigua* ATCC 22034; and sugar in an amount between 1 to 3% (w/w of flour), more preferably about 2% (w/w of flour) and/or amyloglucosidase in an amount between 0.1 to 3 AGU/g flour, more preferably between 0.30 to 1.5 AGU/g flour, even more preferably between 0.3 to 0.75 AGU/g flour leavening the dough; and baking the dough.

Preferably the dough contains between $10^7$ to $10^9$ CFU/g of said strains of the genus *Kazachstania* and/or *Lachancea*, in particular strains of the genus *Kazachstania*, and more preferably between $10^8$ to $10^9$ cfu/g based on the weight of flour.

The sugar is any sugar fermentable by the yeast strain present in the leavening agent. Preferably the sugar is sucrose or glucose, more preferably sucrose.

In specific embodiments the strain(s) of the genus *Kazachstania* and/or *Lachancea* is(are) added to the dough under the form of a liquid leavening agent or a dried leavening agent. Preferably the dough contains between 0.3 and 2% of a liquid leavening agent (calculated as dried weight liquid leavening agent/weight flour) characterized by having:

an amount of *Kazachstania* and/or *Lachancea* cells between about $10^8$ to $10^{10}$ cfu/ml;

a pH between about 3.9 and about 4.8; and;

a leavening power between about 300 ml and about 1500 ml of $CO_2$ produced in 2 hours when measured by SJA analysis, preferably between about 600 ml and about 1300 ml. Preferably, the leavening agent contains amyloglucosidase in an amount to give an activity between 1 and 30 AGU/g, preferably between 3 and 15 AGU/g, even more preferably between 3 and 7.5 AGU/g.

According to a further aspect, the present invention relates to a baked product comprising a composition as described herein. Preferably said baked product is a bakery or patisserie product comprising the composition according to the present invention.

The method of the present invention allows obtaining bread with new pleasant aroma and taste. It is therefore another embodiment of the present invention to provide baked products obtained by the method of the invention. The baked product is a leavened baked product, the major ingredient of which being flour derived from cereal grains. The baked product may contain fat or fat replacer, sugar, eggs, gluten, starch, hydrocolloids, enzymes, emulsifiers, oxidizing or reducing compounds, prebiotics compounds and/or an improver. Non-limiting examples of baked products are bread, baguettes, rolls, soft rolls, donuts, buns, microwavable buns, Danish pastry, hamburger rolls, pizza and pita bread.

The aroma and the taste of the breads may be evaluated by several techniques.

A method to evaluate the aroma of the breads is to analyze their content in volatile compounds by performing a SPME-GC/MS (Solid Phase Microextraction coupled to Gas chromatography and Mass Spectroscopy). Typically the breads according to the invention or obtained by the method of the invention have a higher content in molecules responsible for the sweet, fruity, floral, nutty and/or acidic aromas. Examples of such molecules are Ethyl acetate; Ethanol; Ethyl isobutyrate; Ethyl butanoate; Isoamyl acetate; Pentanoic acid, ethyl ester; Pentanoic acid, 4-methyl-, ethyl ester; Isoamyl alcohol; Hexanoic acid, ethyl ester; 3-buten-1-ol, 3-methyl; Butanoic acid, pentyl ester; Butanoic acid, 4-pentenyl ester; Methylpyrazine; Hex-4-enoic acid ethyl ester; 2-Buten-1-ol, 3-methyl; Pyrazine, 2-ethyl-6-methyl; Pyrazine, 2-ethyl-5-methyl; Pyrazine, 2-ethyl-3-methyl; Octanoic acid, ethyl ester; Acetic acid; Acetylfuran; 2-methylpropionic acid; Sorbic acid; Butanoic acid; 2-furanmethanol; 3-methylbutanoic acid; Pentanoic acid; 4-methylpentanoic acid; Acetic acid, 2-phenylethyl ester; Hexanoic acid; Phenyl ethyl alcohol; Maltol.

An alternative method to evaluate the aroma, flavour and/or the taste of baked products is to let these be evaluated by a taste panel. This method uses a panel of expert people trained to describe and discriminate aroma, flavours and tastes of baked products. In particular, they are asked to detect and describe off-flavours.

In yet a further aspect, the present invention provides in a *Kazachstania bulderi* strain deposited under accession number MUCL 54530 at the BCCM/MUCL (Agro)industrial Fungi & Yeasts Collection, or a *Lachancea thermotolerans* strain deposited under accession number MUCL 55817 at the BCCM/MUCL (Agro)industrial Fungi & Yeasts Collection.

TABLE A1

Indications relating to deposited microorganism
*Kazachstania bulderi* MUCL 54530

| | |
|---|---|
| Accession number given by depositary institution | MUCL 54530 |
| Identification reference given by the depositor | SE3 |
| Name of depositary institution | Belgian Coordinated Collections of Microorganisms BCCM/MUCL |
| Address of depositary institution | Université Catholique de Louvain (UCL) Laboratory of Mycology Place Croix du Sud; 3 B-1348 Louvain-la-Neuve Belgium |
| Date of deposit | Jan. 8, 2013 |
| Name of depositor | PURATOS NV |
| Address of depositor | Industrialaan 25 B-1702 Groot-Bijgaarden Belgium |

TABLE A2

Indications relating to deposited microorganism
*Lachancea thermotolerans* MUCL 55817

| | |
|---|---|
| Accession number given by depositary institution | MUCL 55817 |
| Identification reference given by the depositor | AZSUE2 |
| Name of depositary institution | Belgian Coordinated Collections of Microorganisms BCCM/MUCL |
| Address of depositary institution | Université Catholique de Louvain (UCL) Laboratory of Mycology Place Croix du Sud; 3 B-1348 Louvain-la-Neuve Belgium |
| Date of deposit | Aug. 18, 2015 |
| Name of depositor | PURATOS NV |
| Address of depositor | Industrialaan 25 B-1702 Groot-Bijgaarden Belgium |

In yet a further aspect, the present invention provides in the use of any one of the strains as described herein, for the preparation of a food product, preferably a baked product, more preferably a bakery or patisserie product.

The invention will be described in the following non-limiting examples.

EXAMPLES

Example 1: Leavening Agents

Strains:

*Kazachstania bulderi* (MUCL 54530), *Kazachstania exigua* (ATCC 22034), *Lachancea thermotolerans* (MUCL 55817), and two strains of *Saccharomyces cerevisiae* (regular baker's yeast and organic regular baker's yeast)

Inoculum:

the yeast strains are stored at −70° C. and maintained on solid YPD medium (20 g/l peptone; 10 g/l yeast extract; 20 g/l agar). An isolated colony of each strain is inoculated in a first flask containing 25 mL of liquid YPD medium (20 g/l peptone; 10 g/l yeast extract) and maintained 24 h at 100 rpm and 30° C. 5 ml of this culture are inoculated in two flasks containing 200 mL liquid medium (bacteriological peptone 3.5 g/l; yeast extract 3 g/l; $KH_2PO_4$ 2 g/l; $MgSO_4.7H_2O$ 1.83 g/l; $(NH_4)_2SO_4$ 1 g/l; D-Glucose 20 g/l; sucrose 55 g/l; penicillin 0.0004 g/l; pH=4.8) and maintained 48 h at room temperature under agitation.

The liquid leavening agents are obtained after three successive fermentation steps performed in 15 l fermenter (C10-3K Biostat C-DCU (Sartorius):

1. First step: 10 l of sterile G3 medium (malt extract 50 g/l; sugar beet molasse 60 g/l; $MgSO_4.7H_2O$ 0.0915 g/l, $(NH_4)_2SO_4$ 0.5 g/l, pH=4.7) are inoculated with the previous flasks of yeast at $10^7$ cells/ml of fermentation medium. The fermentation lapses for about 15 to 20 hours in batch culture mode with an air flow of 17 l/min at pH 4.7 and at 30° C. The amount of biomass depends on the yeast strain and on its growth performances. Typical amount of *Kazachstania bulderi* biomass is between 4 and 10 g dry matter/l.

After fermentation, the fermentation broth is centrifuged for 5 minutes at 5000 rpm in a Avanti™ J-20 centrifuge (Beckman Coulter) and washed 2 times with cold water. The pellet (Fresh yeast≈30% dry matter) is resuspended in a volume of water to obtain a cream yeast with a dry matter of about 20%.

2. Second step: cream yeast of the first fermentation step (amount equivalent to about 3.7 to 4.6 g of yeast dry matter/litre) is used to inoculate the next fermentation. The second fermentation lapses for about 15 hours in fed-batch culture mode with an air flow of 7.5 l/min, at 30° C. and a pH between 3.9 and 6 chosen according to the yeast strain characteristics. During the fermentation, the sugar source (cereal hydrolysate), the nitrogen source $NH_4(OH)$ (6.25% solution) and the phosphorus source $H_3PO_4$ (17.8% solution) are fed progressively into the bioreactor. Vitamins and minerals amounts are adjusted according to the yeast strains requirements. Solutions of $H_2SO_4$ (5%), of NaOH (29%) and of anti-foam allow respectively the regulation of pH and the prevention of foam formation. The amount of biomass at the end of the fermentation depends on the strain type and on its ability to grow. Typical amount of *Kazachstania bulderi* biomass at the end of the second step is between 25 and 35 g yeast dry matter/l. At the end of the fermentation, cells are recovered and washed as described above.

3. Third step: cream yeast of the second fermentation step (amount equivalent to about 8.3 g of yeast dry matter/litre) is used to inoculate the final fermentation. The fermentation lapses for about 15 hours in fed-batch culture mode with an air flow of 7.5 l/min, at 30° C. and a pH between 3.9 and 6 chosen according to the yeast strain characteristics. During the fermentation, the sugar source (cereal hydrolysate), the nitrogen source $NH_4(OH)$ and the phosphorus source $H_3PO_4$ are fed progressively into the bioreactor. Vitamins and minerals amounts are adjusted according to the yeast strains requirements. Solutions of $H_2SO_4$ (5%), of NaOH (29%) and of anti-foam allow respectively the regulation of pH and the prevention of foam formation. The amount of biomass at the end of the fermentation depends on the strain type and on its ability to grow. Typical amount of *Kazachstania bulderi* biomass is between 40 and 75 g yeast dry matter/l.

The yeast biomass of the liquid leavening agent is determined as follows: a known mass or volume of liquid leaven is centrifuged during 15 minutes (Avanti™ J-20, BECK-MAN COULTER), at 7000 rpm and 4° C. The supernatant is discarded. The yeast layer at the surface of the pellet is recovered by scraping and weighed to determine the wet biomass. Dry matter is determined by after drying the recovered yeast in an oven at 105° C. for 24 hours.

Leavening Power

The leavening power of the samples is measured by the SJA method. Doughs are made with 280 g wheat flour (DUO, Ceres, Belgium), leavening agent or yeast in an amount corresponding to 1.37 g of yeast dry matter, 5.04 g of NaCl and water up to a total dough hydration level of 35%. For leavening agents with *Kazachstania bulderi*, 0.75 AGU/g flour of amyloglucosidase is added to the dough. Doughs are mixed during 6 minutes in a farinograph (SCHMERSAL) at 30° C. 300 g of dough are introduced into a SJA fermentograph (Mekab machine, Mekab i Nässjö AB) chamber at 37° C. The $CO_2$ production is measured during two hours with an intermediate mixing step after one hour.

The SJA (expressed in ml $CO_2$) is calculated according to the following formula:

$$SJA \text{ (ml } CO_2) = \frac{(V_1 + V_2) \times P_r}{1013}$$

wherein $V_1$ is the volume of $CO_2$ produced after 1 hour, $V_2$ the volume of $CO_2$ produced during the 2nd hour and $P_r$ the real air pressure (mb/hPa).

TABLE 1

| SJA results | |
| --- | --- |
| | ml $CO_2$ |
| Leavening agent based on fermentation of rye malt flour hydrolysate by *Kazachstania bulderi* MUCL 54530 | 676 |
| Leavening agent based on fermentation of rye malt flour hydrolysate by *Saccharomyces cerevisiae* | 800 |

A leavening agent obtained by the fermentation of a cereal hydrolysate by a strain of *Kazachstania bulderi* has a comparable fermentation power than a leavening agent obtained by the fermentation of a cereal hydrolysate by a strain of *Saccharomyces cerevisiae*.

Example 2: Baking Tests

Country breads were made using different liquid leavening agents obtained by the method of example 1. The properties of the leavening agents are shown in table 2 and the compositions of the bread doughs are shown in table 3.

TABLE 2

| liquid leavening agents composition | | | |
| --- | --- | --- | --- |
| Leavening agent | Yeast strain | Cereal hydrolysate | yeast dry matter (g/g leavening agent) |
| L1 | *Kazachstania bulderi* MUCL 54530 | Rye malt flour hydrolysate | 7.5 |
| L2 | *Kazachstania bulderi* MUCL 54530 | Wheat flour hydrolysate | 7.5 |

TABLE 2-continued

| | | | yeast dry matter (g/g |
|---|---|---|---|
| Leavening agent | Yeast strain | Cereal hydrolysate | leavening agent) |
| L3 | *Saccharomyces cerevisiae* (regular baker's yeast) | Rye malt flour hydrolysate | 7.5 |
| L4 | *Saccharomyces cerevisiae* (regular baker's yeast) | Wheat flour hydrolysate | 7.5 |

TABLE 3 doughs composition

| | Breads | | | |
|---|---|---|---|---|
| Ingredient (baker's %) | 1 | 2 | 3 | 4 |
| Wheat flour | 100 | 100 | 100 | 100 |
| Water | 55 | 55 | 55 | 55 |
| L1 | 10 | — | — | — |
| L2 | — | 10 | — | — |
| L3 | — | — | 10 | — |
| L4 | — | — | — | 10 |
| Amyloglucosidase (500 AGU/g) | 0.15 | 0.15 | — | — |
| Salt | 2 | 2 | 2 | 2 |

The ingredients were mixed for 5 min at low speed and 6 min at high speed in a dough mixer (Diosna SP24). Temperature in the bakery was about 25° C. and humidity about 55%. Water temperature is around 12° C. and dough temperature was about 27° C. After a bulk fermentation for 20 min at room temperature the doughs were divided in 800 g pieces, shaped in a round form and submitted to a final proofing step in a Koma fermentation room (70 min, 30° C., 90% relative humidity) before baking at 230° C. for 35 min with steam in a Miwe Condo oven.

Bread Volume

After baking the volume of the breads is measured by the rapeseeds displacement method. Values given are the mean value of 4 measurements.

TABLE 3

| Breads | Volume (mL) |
|---|---|
| 1 | 2425 |
| 2 | 2400 |
| 3 | 2450 |
| 4 | 2425 |

The use of liquid leavening agents based on *Kazachstania bulderi* instead of *Saccharomyces cerevisiae* does not impact the volume of breads.

Bread Flavour

Breads 1 to 4 were presented to a panel of 5 expert judges trained to evaluate taste and flavour of baked products. They were asked to describe the flavour of the breads.

All judges perceived a difference in flavour between the bread 1 and 2 compared to the breads 3 and 4.

Furthermore all judges detected unanimously an off-flavour in the breads prepared and baked with a liquid leavening agent based on the fermentation of a cereal hydrolysate by *Saccharomyces cerevisiae* (rye malt flour or wheat flour hydrolysate—breads 3 and 4). This off-flavour was described as bitter and having a flavour of wet straw.

No off flavour is observed with liquid leavening agents based on the fermentation of cereal hydrolysates by *Kazachstania bulderi*.

Example 3: Characterisation of Aroma

A series of liquid leavening agents have been prepared according to the method of example 1 using different yeast strains and different carbon sources. Their compositions and properties are summarized in Table 4.

TABLE 4 liquid leavening agents composition

| Leavening agent | Yeast strain | Carbon source |
|---|---|---|
| Kb2 | *Kazachstania bulderi* MUCL 54530 | Rye malt flour hydrolysate |
| Kb3 | *Kazachstania bulderi* MUCL 54530 | Wheat flour hydrolysate |
| Ke2 | *Kazachstania exigua* | Rye malt flour hydrolysate |
| Ke3 | *Kazachstania exigua* | Wheat flour hydrolysate |
| Ag2 | *Saccharomyces cerevisiae* (organic regular baker's yeast) | Rye malt flour hydrolysate |
| Ag3 | *Saccharomyces cerevisiae* (organic regular baker's yeast) | Wheat flour hydrolysate |
| Lt2 | *Lachancea thermotolerans* MUCL 55817 | Rye malt flour hydrolysate |
| Sc2 | *Saccharomyces cerevisiae* (regular baker's yeast) | Rye malt flour hydrolysate |
| Sc3 | *Saccharomyces cerevisiae* (regular baker's yeast) | Wheat flour hydrolysate |

Breads were prepared using these leavening agents as in example 2.

Comparison of Flavours by MS-Nose Technology

The aromas of the liquid leavening agents and of the breads were analysed by MS-nose technology. MS-nose configuration consisted of a gas chromatograph-mass spectrometer HP 7890A/5975C (Agilent Technologies®) equipped with an MPS-2W autosampler (Gersten. Chem-Sensor® software (G1701BA, Version B.01.00, Agilent Technologies®) and The Unscrambler® multivariate analysis software (9.8, Camo®, Oslo, Norway) were loaded into the GC-MS system.

A sample weight of 1 g of each leavening agent and of each bread was weighed in a 20 ml glass vial, which was closed with a magnetic cap with a silicone/PTFE septum. The samples were preheated for 10 min. at 40° C. and the volatiles molecules were extracted by SPME (Fibre type DVB/CAR/PDMS Supelco Gray® 57329-U) for 30 min at equal temperature. After HS-SPME isolation, the splitless thermal desorption of the leavening agent and bread volatiles from the fibre was performed for 5 min at 250° C. in the GC injector. The GC column (RESTEK Stabilwax columns (fused silica)) was maintained at 250° C. (no separation of volatiles), and helium was used as carrier gas (1 ml/min). Analysis is carried out 2 times per sample. The TIC (total ion current) of each samples lead to a total mass spectrum that is converted by the ChemSensor® software to a mass fingerprint, which could be easily imported in the Unscrambler 9.8 (Camo®, Oslo, Norway).

PCA (Principal Component Analysis) was performed on the MS-nose results, of which all data were normalized to 100.

Both liquid leavening agents and breads were analysed separately. Furthermore the samples were compared based on the carbon source used in order to obtain the strain effect on the aroma.

For each type of sample three groups of strains were identified. The results are summarized in table 5 (liquid leavening agents) and table 6 (breads) respectively.

TABLE 5

| Groups obtained by the PCA analysis of the MS-nose profiles obtained with the liquid leavening agents | | |
| --- | --- | --- |
| Carbon source | Rye malt flour hydrolysate | Wheat flour hydrolysate |
| Group I | Kb2, Ke2 | Kb3 |
| Group II | Lt2 | Ke3 |
| Group III | Ag2, Sc2 | Ag3, Sc3 |

TABLE 6

| Groups obtained by the PCA analysis of the MS-nose profiles obtained with the breads | | |
| --- | --- | --- |
| Carbon source | Rye malt flour hydrolysate | Wheat flour hydrolysate |
| Group I | Ke2 | Ke3 |
| Group II | Lt2 | Kb3, Ag3 |
| Group III | Ag2, Sc2 | Sc3 |

The use of *Kazachstania* strains, in particular strains of *Kazachstania bulderi* in the leavening agents according to the invention allows to obtain new and specific aroma.

Comparison of Aromas by SPME-GC-MS

The content in volatile molecules of two samples of liquid leavening agents have been compared by SPME-GC-MS (solid phase microextraction (SPME) and gas chromatography-mass spectrometry (GC-MS). The two samples were Kb2 (rye malt flour hydrolysate fermented by *Kazachstania bulderi* MUCL 54530) and Sc2 (rye malt flour hydrolysate fermented by *Saccharomyces cerevisiae*).

HS-SPME-GC-MS configuration consisted of a gas chromatograph-mass spectrometer HP 7890A/5975C (Agilent Technologies®) equipped with an MPS-2W autosampler (Gersten. ChemSensor® software (G1701BA, Version B.01.00, Agilent Technologies®) and The Unscrambler® multivariate analysis software (9.8, Camo®, Oslo, Norway) were loaded into the GC-MS system.

A sample weight of 1 g of each leavening agent was weighed in a 20 ml glass vial, which was closed with a magnetic cap with a silicone/PTFE septum. The samples were preheated for 10 min at 40° C. and the volatile molecules were extracted by SPME (Fibre type DVB/CAR/PDMS Supelco Gray ° 57329-U) for 30 min at equal temperature. After HS-SPME isolation, the splitless thermal desorption of the leavening agents from the fibre was performed for 5 min at 250° C. in the GC injector (SPME liner of 0.75 mm i.d.). The GC column (RESTEK Stabilwax columns (fused silica)) was maintained at 40° C. for 7 min, and then programmed at a rate of 16° C./min to a temperature of 230° C., which was held for 8 min. Helium was used as carrier gas (1 ml/min). Injector and detector (MS-source) were kept at 240° C. and 230° C., respectively. The mass spectra were measured by electron impact of 70 eV. The TIC (total ion current) chromatograms were recorded by monitoring in a mass-to-charge ratio (m/z) range of 40-180 amu. The identification of volatiles was made by comparing the mass spectra of the different components to those in a Mass Spectral Library Wiley275® (J. Wiley & Sons LTD®).

The result of the analysis is depicted on FIG. 1. It shows that the aromatic profiles of the two liquid leavening agents are very different. The table 7 describes some of the molecules present in Kb2 and that are absent or in a very small quantity in Sc2. This cocktail of molecules is typical of a mixture giving a fruity note.

TABLE 7

| Retention time (min) | Molecule |
| --- | --- |
| 5.386 | Ethanol |
| 9.830 | Hexanal |
| 12.410 | 3-buten-1-ol, 3-methyl |
| 14.604 | Acetic acid |
| 14.790 | Furfural |
| 15.417 | Benzaldehyde |

Aromatic Profile of a Bread Obtained with a Liquid Leavening According to the Invention The content in volatile molecules of breads prepared with Kb2 (rye malt flour hydrolysate fermented by *Kazachstania bulderi* MUCL 54530) or Sc2 (rye malt flour hydrolysate fermented by *Saccharomyces cerevisiae*) as leavening agent has been determined by SPME-GC-MS.

Samples were prepared and analysed as for the liquid leavening agents.

Figure 2:
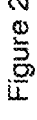
FIG. 2 shows a comparison of the content in volatile molecules obtained by SPME-GC-MS of breads prepared with Kb2 (rye malt flour hydrolysate fermented by Kazachstania *bulderi* MUCL 54530-lower part of the graph) and of breads prepared with Sc2 (rye malt flour hydrolysate fermented by *Saccharomyces cerevisiae*-upper part of the graph).

The results of the analysis are presented on FIG. 2. The aromatic profile of the bread made with Kb2 is more rich and complex than the one of bread made with Sc2. The table 8 describes some of the molecules present in bread made with Kb2 and that are absent or in a very small quantity in bread made with Sc2. These molecules are typically responsible for sweet, fruity, floral, nutty and/or acidic aromas.

TABLE 8

| Retention time (min) | Molecule |
| --- | --- |
| 4.104 | Ethyl acetate |
| 5.344 | Ethanol |
| 6.389 | Ethyl isobutyrate |
| 8.818 | Ethyl butanoate |
| 10.524 | Isoamyl acetate |
| 10.733 | Pentanoic acid, ethyl ester |
| 11.591 | Pentanoic acid, 4-methyl-, ethyl ester |
| 11.873 | Isoamyl alcohol |
| 12.178 | Hexanoic acid, ethyl ester |
| 12.436 | 3-buten-1-ol, 3-methyl |
| 12.565 | Butanoic acid, pentyl ester |
| 12.627 | Butanoic acid, 4-pentenyl ester |
| 12.724 | Methylpyrazine |
| 12.903 | Hex-4-enoic acid ethyl ester |
| 13.221 | 2-Buten-1-ol, 3-methyl |
| 13.988 | Pyrazine, 2-ethyl-6-methyl |
| 14.060 | Pyrazine, 2-ethyl-5-methyl |
| 14.184 | Pyrazine, 2-ethyl-3-methyl |
| 14.336 | Octanoic acid, ethyl ester |
| 14.593 | Acetic acid |
| 15.169 | Acetylfuran |
| 15.571 | 2-methylpropionic acid |
| 15.740 | Sorbic acid |
| 16.061 | Butanoic acid |
| 16.299 | 2-furanmethanol |
| 16.381 | 3-methylbutanoic acid |
| 16.903 | Pentanoic acid |
| 17.376 | 4-methylpentanoic acid |
| 17.591 | Acetic acid, 2-phenylethyl ester |
| 17.673 | Hexanoic acid |
| 18.266 | Phenyl ethyl alcohol |
| 18.715 | Maltol |

The invention claimed is:

1. A leavening agent comprising cereal hydrolysates, wherein said leavening agent is fermented by a Kazachstania bulderi strain and optionally one or more strain(s) of the genus Lachancea, wherein the leavening power of said leavening agent ranges between about 300 ml and about 1500 ml of $CO_2$ produced in 2 hours when measured by SJA analysis.

2. A method for producing a leavening agent, comprising fermenting a mixture comprising cereal hydrolysates, and a liquid with at least a Kazachstania *bulderi* strain and optionally one or more strain(s) of the genus Lachancea, thereby obtaining a leavening agent, and optionally stabilizing and/or packaging said leavening agent, wherein the leavening power of said leavening agent ranges between about 300 ml and about 1500 ml of $CO_2$ produced in 2 hours when measured by SJA analysis.

3. The leavening agent according to claim 1, wherein at least one of said strains of the genus Lachancea is a strain of Lachancea *thermotolerans*.

4. The leavening agent according to claim 1, wherein said Kazachstania *bulderi* strain is Kazachstania *bulderi* MUCL 54530 and, optionally, wherein at least one of said strains of the genus Lachancea is Lachancea *thermotolerans* MUCL 55817.

5. The leavening agent according to claim 1, comprising (a) an amount of a Kazachstania *bulderi* strain and optionally one or more strain(s) of the genus Lachancea ranging between about $10^8$ to $10^{10}$ cfu/ml, and/or (b) wherein the pH of said leavening agent ranges between about 3.8 and about 6.

6. The leavening agent according to claim 1, wherein said Kazachstania *bulderi* strain and optionally one or more strain(s) of the genus Lachancea are combined with one or several other strain(s) of microorganisms.

7. The leavening agent according to claim 1, wherein said Kazachstania *bulderi* strain and optionally one or more strain(s) of the genus Lachancea are essentially the sole $CO_2$ producing microorganism in said leavening agent.

8. The leavening agent according to claim 1, wherein said leavening agent comprises an amylase source.

9. The leavening agent according to claim 1, wherein said cereal hydrolysates are based on durum wheat flour or durum wheat malt, on wheat flour or wheat malt, on rye flour or rye malt or on a combination of these.

10. A baked product comprising a composition comprising cereal hydrolysates, wherein said composition is at least fermented by a Kazachstania *bulderi* strain and optionally one or more strain(s) of the genus Lachacea, optionally wherein:

at least one of said strains of the genus Lachancea is a strain of Lachancea *thermotolerans;* said Kazachstania *bulderi* strain is Kazachstania *bulderi* MUCL 54530 and, optionally, wherein at least one of said strains of the genus Lachancea is Lachancea *thermotolerans* MUCL 55817;

said composition comprises (a) an amount of a Kazachstania *bulderi* strain and optionally one or more strain (s) of the genus Lachancea ranging between about $10^8$ to $10^{10}$ cfu/ml; (b) wherein the pH of said composition ranges between about 3.8 and about 6; and/or (c) wherein the leavening power of said composition ranges between about 300 ml and about 1500 ml of $CO_2$ produced in 2 hours when measured by SJA analysis;

said Kazachstania *bulderi* strain and optionally one or more strain(s) of the genus Lachancea are combined with one or several other strain(s) of microorganisms, optionally other strain(s) of yeast and/or strains of lactic acid bacteria;

said Kazachstania *bulderi* strain and optionally one or more strain(s) of the genus Lachancea are essentially the sole $CO_2$ producing microorganism in said composition;

said composition comprises an amylase source optionally chosen from the group of amyloglucosidase, malt active flour and alpha-amylase, wherein the source of amylase is optionally added in an amount to obtain in said composition between 1 and 30 AGU/g liquid leaven of amyloglucosidase; between 1 and 16 DU/g liquid leaven of active malt flour; or between 10 and 80 SKB/g liquid leaven of alpha-amylase; and/or said cereal hydrolysates are based on durum wheat flour or durum wheat malt, on wheat flour or wheat malt, on rye flour or rye malt or on a combination of these;

optionally wherein said baked product is a bakery or patisserie product comprising a composition comprising cereal hydrolysates, wherein said composition is at least fermented by a Kazachstania *bulderi* strain and optionally one or more strain(s) of the genus Lachacea.

11. A method for obtaining a baked product, optionally a bakery or patisserie product, comprising the steps of:

providing a composition comprising cereal hydrolysates, wherein said composition is at least fermented by a Kazachstania *bulderi* strain and optionally one or more strain(s) of the genus Lachacea; optionally wherein:

at least one of said strains of the genus Lachancea is a strain of Lachancea *thermotolerans;* said Kazachstania *bulderi* strain is Kazachstania *bulderi* MUCL 54530 and, optionally, wherein at least one of said strains of the genus Lachancea is Lachancea *thermotolerans* MUCL 55817;

said composition comprises (a) an amount of a Kazachstania *bulderi* strain and optionally one or more strain (s) of the genus Lachancea ranging between about $10^8$ to $10^{10}$ cfu/ml; (b) wherein the pH of said composition ranges between about 3.8 and about 6; and/or (c) wherein the leavening power of said composition ranges between about 300 ml and about 1500 ml of $CO_2$ produced in 2 hours when measured by SJA analysis;

said Kazachstania *bulderi* strain and optionally one or more strain(s) of the genus Lachancea are combined with one or several other strain(s) of microorganisms, optionally other strain(s) of yeast and/or strains of lactic acid bacteria;

said Kazachstania *bulderi* strain and optionally one or more strain(s) of the genus Lachancea are essentially the sole $CO_2$ producing microorganism in said composition;

said composition comprises an amylase source optionally chosen from the group of amyloglucosidase, malt active flour and alpha-amylase, wherein the source of amylase is optionally added in an amount to obtain in said composition between 1 and 30 AGU/g liquid leaven of amyloglucosidase; between 1 and 16 DU/g liquid leaven of active malt flour; or between 10 and 80 SKB/g liquid leaven of alpha-amylase; and/or said cereal hydrolysates are based on durum wheat flour or durum wheat malt, on wheat flour or wheat malt, on rye flour or rye malt or on a combination of these;

adding the composition to a dough or a batter; and baking the dough or the batter, thereby obtaining the baked product, optionally the bakery or patisserie product.

12. The method according to claim 2, wherein at least one of said strains of the genus Lachancea is a strain of Lachancea *thermotolerans*.

13. The method according to claim 2, wherein said Kazachstania *bulderi* strain is Kazachstania *bulderi* MUCL 54530 and, optionally, wherein at least one of said strains of the genus Lachancea is Lachancea *thermotolerans* MUCL 55817.

14. The method according to claim 2, wherein said leavening agent comprises (a) an amount of a Kazachstania *bulderi* strain and optionally one or more strain(s) of the genus Lachancea ranging between about $10^8$ to $10^{10}$ cfu/ml, and/or (b) wherein the pH of said leavening agent ranges between about 3.8 and about 6.

15. The method according to claim 2, wherein said Kazachstania *bulderi* strain and optionally one or more strain(s) of the genus Lachancea are combined with one or several other strain(s) of microorganisms, optionally other strain(s) of yeast and/or strains of lactic acid bacteria.

16. The method according to claim 2, wherein said Kazachstania *bulderi* strain and optionally one or more strain(s) of the genus Lachancea are essentially the sole $CO_2$ producing microorganism in said leavening agent.

17. The method according to claim 2, wherein said leavening agent comprises an amylase source optionally chosen from the group of amyloglucosidase, malt active flour and alpha-amylase, wherein the source of amylase is optionally added in an amount to obtain in said leavening agent between 1 and 30 AGU/g liquid leaven of amyloglucosidase; between 1 and 16 DU/g liquid leaven of active malt flour, or between 10 and 80 SKB/g liquid leaven of alpha-amylase.

18. The method according to claim 2, wherein said cereal hydrolysates are based on durum wheat flour or durum wheat malt, on wheat flour or wheat malt, on rye flour or rye malt or on a combination of these.

19. The leavening agent according to claim 8, wherein said amylase source is selected from the group consisting of amyloglucosidase, malt active flour and alpha-amylase.

20. The leavening agent according to claim 8, wherein said amylase source is added in an amount to obtain in said leavening agent between 1 and 30 AGU/g liquid leaven of amyloglucosidase, between 1 and 16 DU/g liquid leaven of active malt flour, or between 10 and 80 SKB/g liquid leaven of alpha-amylase.

21. The leavening agent according to claim 6, wherein said Kazachstania *bulderi* strain and optionally one or more strain(s) of the genus Lachancea are combined with one or several other strain(s) of yeast and/or strains of lactic acid bacteria.

22. The leavening agent according to claim 1, wherein said leavening agent comprises fermented cereal hydrolysates, wherein said leavening agent comprises a Kazachstania *bulderi* strain and optionally one or more strain(s) of the genus Lachancea, and wherein the cereal hydrolysates are at least fermented by the Kazachstania *bulderi* strain and optionally by the one or more strain(s) of the genus Lachancea.

23. The leavening agent according to claim 1, wherein said leavening agent comprises essentially fermented cereal hydrolysates, wherein said cereal hydrolysates are fermented by a K *bulderi* strain and, optionally, one or more strain(s) of the genus Lachancea.

24. The leavening agent according to claim 1, wherein said leavening agent is a liquid leavening agent.

* * * * *